US009763765B2

(12) United States Patent
Horan et al.

(10) Patent No.: US 9,763,765 B2
(45) Date of Patent: *Sep. 19, 2017

(54) VASCULAR FILTER (71) Applicant: Novate Medical Limited, Dublin (IE)

(72) Inventors: Steven Horan, Galway (IE); Jacquline O'Gorman, County Clare (IE); Aidan Goggin, Galway (IE)

(73) Assignee: Novate Medical Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 14/447,277

(22) Filed: Jul. 30, 2014

(65) Prior Publication Data
US 2015/0025565 A1 Jan. 22, 2015

Related U.S. Application Data (63) Continuation of application No. 13/268,378, filed on Oct. 7, 2011, now Pat. No. 8,821,530, which is a (Continued)

(51) Int. Cl.
A61F 2/01 (2006.01)

(52) U.S. Cl.
CPC .......... A61F 2/01 (2013.01); A61F 2002/016 (2013.01); A61F 2002/018 (2013.01);
(Continued)

(58) Field of Classification Search
CPC ................ A61F 2/01; A61F 2002/016; A61F 2002/018; A61F 2230/005; A61F 2/2475
(Continued)

(56) References Cited

U.S. PATENT DOCUMENTS 4,425,908 A * 1/1984 Simon ................. A61F 2/01
                                              128/899
5,344,427 A   9/1994 Cottenceau et al.
(Continued)

FOREIGN PATENT DOCUMENTS

DE    40 30 998 A1    4/1991
DE    102008031299    1/2010
(Continued)

OTHER PUBLICATIONS

European Search Report for EP Application No. 12075021.1 mailed on Jul. 18, 2012.
(Continued)

Primary Examiner — Kathleen Holwerda
(74) Attorney, Agent, or Firm — Bookoff McAndrews, PLLC (57) ABSTRACT A vascular filter (1) comprises a proximal support hoop (3), a plurality of support struts (5), and a plurality of capture arms (6). The proximal support hoop (3) extends around the internal wall of the inferior vena cava in a wave pattern having six distal peaks (11) and six proximal peaks (11). The proximal support hoop (3) comprises an enlarged end element at each peak (11). The support struts (5) extend longitudinally along the internal wall of the inferior vena cava in a curve (14). Two capture arms (6) are connected to the proximal support hoop (3) at each distal peak (11). Each capture arm 6 extends from the distal peak (11) to an apex (7) in a curve (12, 13). The concave portion of the first curve (12) faces inwardly towards the concave portion of the second curve (13).

16 Claims, 7 Drawing Sheets

Related U.S. Application Data continuation of application No. 12/355,556, filed on Jan. 16, 2009, now Pat. No. 8,057,507.

(52) U.S. Cl.
CPC . *A61F 2210/0004* (2013.01); *A61F 2230/005* (2013.01); *A61F 2230/008* (2013.01)

(58) Field of Classification Search
USPC .............................. 606/200; 623/1.24–1.26
See application file for complete search history.

(56) References Cited

U.S. PATENT DOCUMENTS

| | | | |
|---|---|---|---|
| 5,375,612 | A | 12/1994 | Cottenceau et al. |
| 5,383,887 | A | 1/1995 | Nadal |
| 5,634,942 | A | 6/1997 | Chevillon et al. |
| 5,725,550 | A | 3/1998 | Nadal |
| 5,800,525 | A | 9/1998 | Bachinski et al. |
| 5,853,420 | A | 12/1998 | Chevillon et al. |
| 5,968,071 | A | 10/1999 | Chevillon et al. |
| 6,193,739 | B1 | 2/2001 | Chevillon et al. |
| 6,214,025 | B1 * | 4/2001 | Thistle et al. ............... 606/200 |
| 6,241,746 | B1 | 6/2001 | Bosma et al. |
| 6,248,128 | B1 | 6/2001 | Berry et al. |
| 6,267,776 | B1 | 7/2001 | O'Connell |
| 6,312,461 | B1 | 11/2001 | Unsworth et al. |
| 6,391,045 | B1 | 5/2002 | Kim et al. |
| 6,482,227 | B1 | 11/2002 | Solovay |
| 6,517,559 | B1 | 2/2003 | O'Connell |
| 6,527,962 | B1 | 3/2003 | Nadal |
| 6,582,447 | B1 | 6/2003 | Patel et al. |
| 6,605,111 | B2 | 8/2003 | Bose et al. |
| 6,635,083 | B1 | 10/2003 | Cheng et al. |
| 6,652,558 | B2 | 11/2003 | Patel et al. |
| 6,666,882 | B1 | 12/2003 | Bose et al. |
| 6,669,721 | B1 | 12/2003 | Bose et al. |
| 6,685,739 | B2 | 2/2004 | DiMatteo et al. |
| 6,852,076 | B2 | 2/2005 | Nikolic et al. |
| 6,881,218 | B2 | 4/2005 | Beyer et al. |
| 6,932,832 | B2 | 8/2005 | Patel et al. |
| 6,966,923 | B2 | 11/2005 | Gittings |
| 6,972,025 | B2 | 12/2005 | WasDyke |
| 7,001,424 | B2 | 2/2006 | Patel et al. |
| 7,094,248 | B2 | 8/2006 | Bachinski et al. |
| 7,261,731 | B2 | 8/2007 | Patel et al. |
| 7,279,007 | B2 | 10/2007 | Nikolic et al. |
| 7,329,269 | B2 * | 2/2008 | Shapiro et al. ............... 606/200 |
| 7,534,251 | B2 | 5/2009 | WasDyke |
| 8,025,675 | B2 * | 9/2011 | Shirley et al. ............... 606/200 |
| 8,057,507 | B2 * | 11/2011 | Horan et al. ............... 606/200 |
| 8,162,970 | B2 | 4/2012 | Gilson et al. |
| 2001/0044652 | A1 | 11/2001 | Moore |
| 2003/0120303 | A1 | 6/2003 | Boyle et al. |
| 2003/0176888 | A1 | 9/2003 | O'Connell |
| 2003/0208227 | A1 | 11/2003 | Thomas |
| 2004/0019374 | A1 | 1/2004 | Hojeibane et al. |
| 2004/0059373 | A1 * | 3/2004 | Shapiro et al. ............... 606/200 |
| 2004/0186550 | A1 * | 9/2004 | Bonsignore ............... A61F 2/91 623/1.15 |
| 2004/0220611 | A1 | 11/2004 | Ogle |
| 2005/0096735 | A1 | 5/2005 | Hojeibane et al. |
| 2005/0107822 | A1 | 5/2005 | WasDyke |
| 2005/0165442 | A1 * | 7/2005 | Thinnes ............... A61F 2/01 606/200 |
| 2005/0222604 | A1 | 10/2005 | Schaeffer |
| 2005/0234504 | A1 | 10/2005 | WasDyke |
| 2006/0025852 | A1 | 2/2006 | Armstrong et al. |
| 2007/0032816 | A1 | 2/2007 | O'Connell et al. |
| 2007/0112372 | A1 | 5/2007 | Sosnowski et al. |
| 2007/0203571 | A1 | 8/2007 | Kaplan et al. |
| 2008/0027481 | A1 | 1/2008 | Gilson et al. |
| 2008/0188887 | A1 * | 8/2008 | Batiste ............... A61F 2/01 606/200 |
| 2008/0208245 | A1 | 8/2008 | Hoffman |
| 2008/0281396 | A1 | 11/2008 | Ishida et al. |
| 2009/0198270 | A1 * | 8/2009 | McGuckin, Jr. ......... A61F 2/01 606/200 |
| 2010/0185229 | A1 | 7/2010 | Horan et al. |
| 2010/0185230 | A1 | 7/2010 | Horan et al. |
| 2010/0228281 | A1 | 9/2010 | Gilson et al. |
| 2012/0245620 | A1 | 9/2012 | Gilson et al. |

FOREIGN PATENT DOCUMENTS

| | | |
|---|---|---|
| EP | 0 565 395 A1 | 10/1993 |
| EP | 0 582 493 A1 | 2/1994 |
| EP | 0 598 635 A1 | 5/1994 |
| EP | 0 605 276 A1 | 7/1994 |
| EP | 0 655 228 A1 | 5/1995 |
| EP | 0 678 284 A1 | 10/1995 |
| EP | 0 737 451 A1 | 10/1996 |
| EP | 0759 287 A1 | 2/1997 |
| EP | 0 935 975 A1 | 8/1999 |
| EP | 1 103 233 A1 | 5/2001 |
| EP | 1 258 228 A1 | 11/2002 |
| EP | 1 616 530 | 1/2006 |
| FR | 2 718 950 A1 | 10/1995 |
| FR | 2 764 503 A1 | 12/1998 |
| FR | 2 814 670 A1 | 5/2002 |
| WO | WO 00/56390 | 9/2000 |
| WO | WO 00/66031 | 11/2000 |
| WO | WO 01/62184 A2 | 8/2001 |
| WO | WO 02/22048 A2 | 3/2002 |
| WO | WO 2006/020425 A1 | 2/2006 |
| WO | WO 2006/074163 A2 | 7/2006 |
| WO | WO 2006/107939 A1 | 10/2006 |
| WO | WO 2006/116636 A1 | 11/2006 |
| WO | WO 2008/010197 | 1/2008 |

OTHER PUBLICATIONS

European Search Report for EP Application No. 1039 4001 mailed on Apr. 27, 2010.

U.S. Appl. No. 12/688,173, filed Jan. 15, 2010 (72 pages).

* cited by examiner

VASCULAR FILTER

CROSS REFERENCE TO RELATED APPLICATIONS

This application is a continuation of U.S. patent application Ser. No. 13/268,378, filed on Oct. 7, 2011, which is a continuation of U.S. patent application Ser. No. 12/355,556, filed on Jan. 16, 2009, now U.S. Pat. No. 8,057,507, the entireties of all of which are hereby incorporated by reference.

INTRODUCTION

This invention relates to a vascular filter.

STATEMENTS OF INVENTION

According to the invention there is provided a vascular filter comprising:
 one or more capture members for capturing thrombus passing through a blood vessel, and
 one or more support members for supporting the one or more capture members relative to a wall of the blood vessel.

By capturing the thrombus, the filter prevents the thrombus from passing to the heart or lungs, which may cause pulmonary embolism. By supporting the capture members this ensures that the capture members are maintained in the desired location in the blood vessel.

In one embodiment of the invention the capture member is movable from a capturing configuration to an open configuration, in the capturing configuration the capture member being configured to capture thrombus passing through a blood vessel, in the open configuration the capture member being configured to facilitate unrestricted blood flow. Preferably in the capturing configuration the capture member extends towards an apex. Ideally in the capturing configuration the capture member extends towards the apex in a curve.

In another embodiment the support member is movable between a delivery configuration and a deployed configuration.

In one case at least part of the support member is configured to extend circumferentially around a wall of a blood vessel in a wave pattern. Preferably the support member comprises a plurality of connector elements, each connector element connecting a peak of the wave pattern to an adjacent peak of the wave pattern. Ideally the support member comprises an enlarged end element at a peak of the wave pattern. This arrangement results in greater flexibility, in lower strains, and in greater resistance to buckling. Most preferably in the delivery configuration the diameter of curvature of the end element is greater than the distance between adjacent connector elements. The wave pattern of the support member may comprise less than twelve distal peaks. This arrangement results in greater resistance to buckling. Preferably the wave pattern of the support member comprises less than ten distal peaks. Ideally the wave pattern of the support member comprises less than eight distal peaks. The capture member may be connected to the support member at a distal peak of the wave pattern. Preferably a first capture member is connected to the support member at a first distal peak of the wave pattern, and a second capture member is connected to the support member at the first distal peak of the wave pattern. Ideally in the capturing configuration the first capture member extends from the first distal peak of the wave pattern towards the apex in a first curve, and the second capture member extends from the first distal peak of the wave pattern towards the apex in a second curve, the concave portion of the first curve facing inwardly towards the concave portion of the second curve. This arrangement minimises any gap between adjacent capture members, and thus improves filter efficiency.

In another case at least part of the support member is configured to extend longitudinally along a wall of a blood vessel. Preferably the support member is configured to extend longitudinally in a curve. This arrangement minimises any bowing or lift-off of the support member from the wall of the blood vessel. Thus the contact force between the support member and the blood vessel is maximised which enhances resistance to buckling. Most preferably when the filter is deployed externally of a blood vessel, in the open configuration the convex portion of the curve faces radially outwardly. In the open configuration the ratio of R1:R2 may be in the range of from 1:1 to 1.5:1, where
 R1 is the distance of the support member from the central longitudinal axis of the filter at the point along the support member where this distance is at a maximum, and
 R2 is the distance of the support member from the central longitudinal axis of the filter at an end of the support member.

In the capturing configuration the maximum distance between the support member and a wall of a blood vessel may be less than 4 mm. In the capturing configuration the maximum distance between the support member and a wall of a blood vessel may be less than 2 mm.

In one embodiment the radial dimension of the support member is greater than 0.20 mm. This arrangement results in greater resistance to buckling. Preferably the radial dimension of the support member is greater than 0.25 mm. Ideally the radial dimension of the support member is greater than 0.30 mm.

In another embodiment at least part of the support member comprises one or more elongate elements, the width of at least one of the elongate elements being greater than 0.25 mm. This arrangement results in greater resistance to buckling. Preferably the width of the elongate element is greater than 0.30 mm. Ideally the width of the elongate element is greater than 0.35 mm.

BRIEF DESCRIPTION OF THE DRAWINGS

The invention will be more clearly understood from the following description of an embodiment thereof, given by way of example only, with reference to the accompanying drawings, in which.

DETAILED DESCRIPTION

Referring to the drawings there is illustrated a vascular filter 1 according to the invention. The vascular filter 1 is suitable for use as an inferior vena cava filter in the inferior vena cava. The filter 1 is movable from a capturing configuration (FIG. 4) to an open configuration (FIG. 8) upon elapse of a predetermined period of time. In the capturing configuration the filter 1 is configured to capture thrombus passing through the inferior vena cava towards the heart and the lungs. The filter 1 may thus be used to prevent pulmonary embolism. In the open configuration the filter 1 is configured to facilitate unrestricted blood flow.

Figure 1:
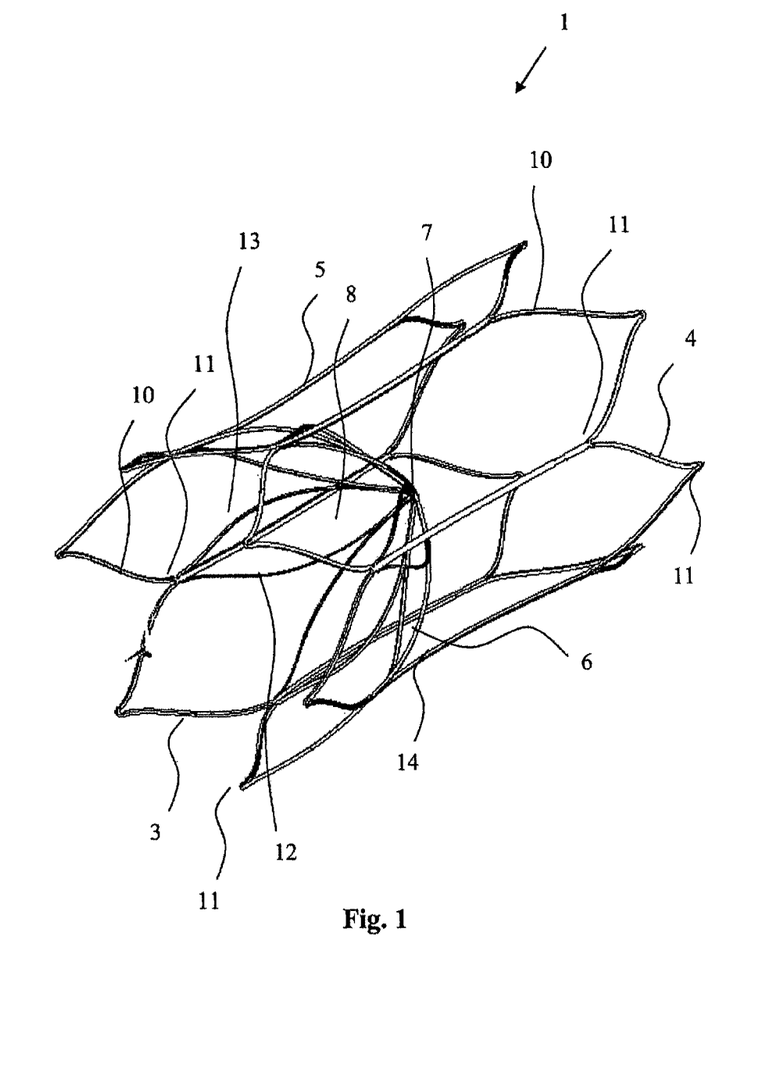
FIG. 1 is an isometric view of a vascular filter according to the invention in a deployed capturing configuration.
Figure 2:
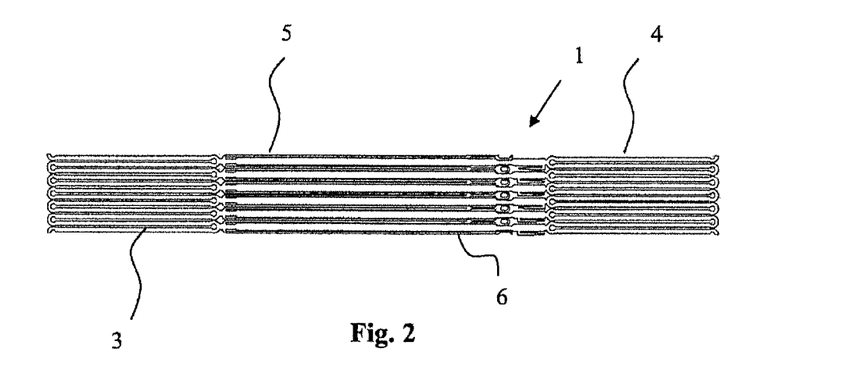
FIG. 2 is a developed side view of the vascular filter of FIG. 1 in a delivery configuration.
Figure 3:
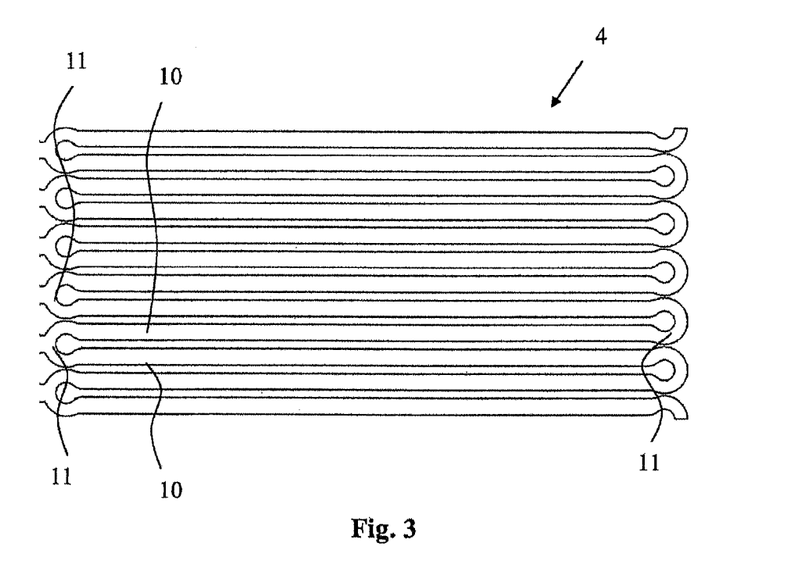
FIG. 3 is an enlarged developed side view of part of the vascular filter of FIG. 2 in the delivery configuration.
Figure 4:
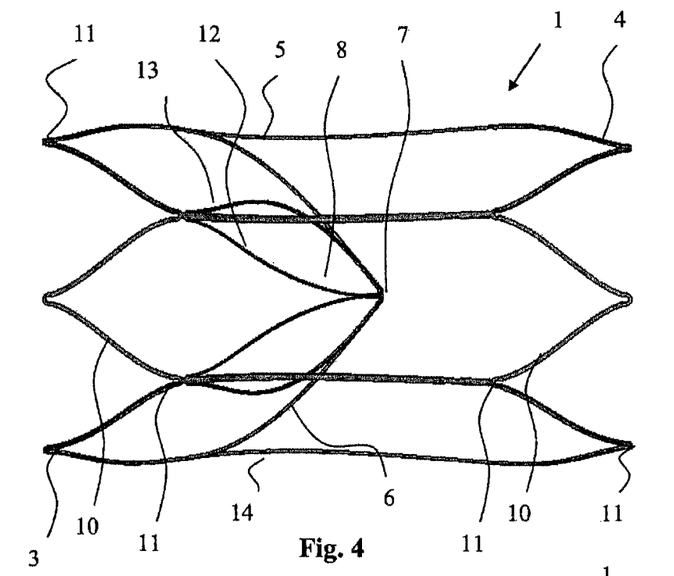
FIG. 4 is a side view of the vascular filter of FIG. 1 in the deployed capturing configuration.

The filter 1 is movable between a collapsed delivery configuration (FIGS. 2 and 3) and an expanded deployed configuration (FIGS. 1 and 4). The filter 1 is biased radially outwardly towards the deployed configuration.

As illustrated in FIG. 1, the filter 1 comprises a proximal support hoop 3 at the proximal end of the filter 1, a distal support hoop 4 at the distal end of the filter 1, and a plurality of support struts 5 extending between the proximal support hoop 3 and the distal support hoop 4.

In this patent specification, the term 'proximal' will be understood to mean the end closest to a user when carrying out a procedure accessed from a femoral vein, or the caudal end. Similarly the term 'distal' will be understood to mean the end furthest from a user when carrying out a procedure accessed from a femoral vein, or the cranial end.

Figure 5:
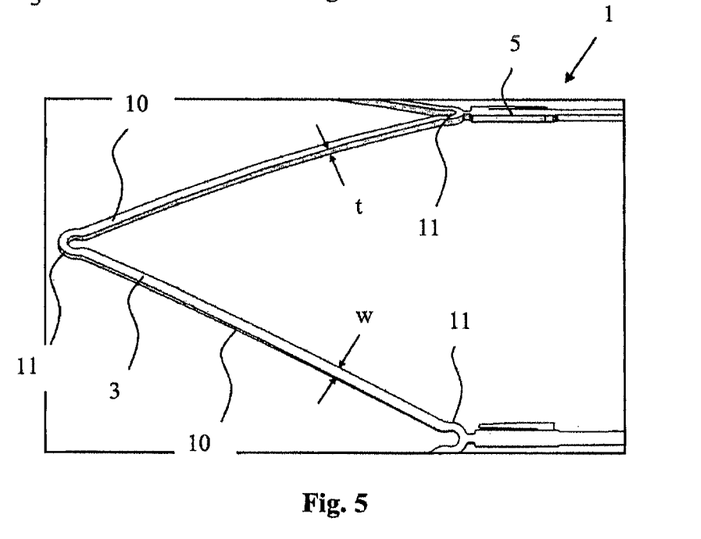
FIG. 5 is an enlarged side view of part of the vascular filter of FIG. 4 in the deployed capturing configuration.
Figure 6:
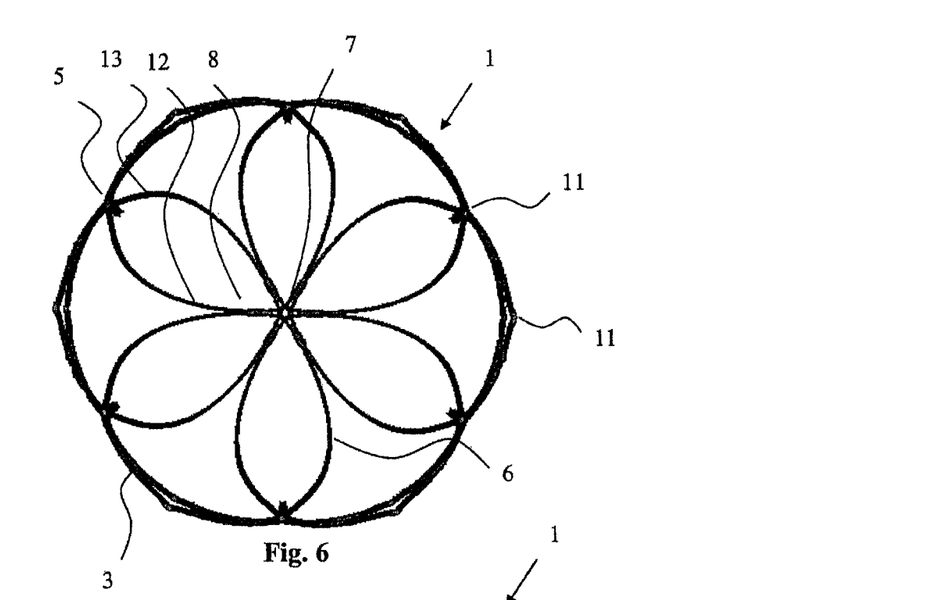
FIG. 6 is an end view of the vascular filter of FIG. 1 in the deployed capturing configuration.

The proximal support hoop 3 extends circumferentially around the internal wall of the inferior vena cava in a zig-zag wave pattern. As illustrated in FIG. 5, the proximal support hoop 3 comprises a plurality of elongate connector elements 10. Each connector element 10 connects a peak 11 of the wave pattern to an adjacent peak 11 of the wave pattern.

In this case the wave pattern of the proximal support hoop 3 comprises six distal peaks 11 and six proximal peaks 11. It has been found that the filter 1 having six distal peaks 11 and six proximal peaks 11 is particularly resistant to buckling.

The proximal support hoop 3 comprises an enlarged end element at each peak 11 of the wave pattern. In the delivery configuration the diameter of curvature of the end element 11 is greater than the distance between adjacent connector elements 10. The geometry of the crown tips 11 allows for less rigid movement of the proximal support hoop 3 and also allows for lower strains in the proximal support hoop 3. Enhanced flexibility of the crown 3 minimises the probability of budding. The crown 3 of the filter 1 offers increased torsional flexibility. This flexibility helps to minimise the probability of buckling.

As illustrated in FIG. 5, the radial dimension or wall thickness t of the proximal support hoop 3 is 0.33 mm in this case. It has been found that the filter 1 has a greater resistance to buckling and a higher radial force. The width w of each connector element 10 is 0.38 mm in this case. The filter 1 with six distal peaks 11 and six proximal peaks 11 has a particularly low profile in the delivery configuration. This low profile enables larger strut thickness t and width w for a given delivery profile.

Similarly the distal support hoop 4 extends circumferentially around the internal wall of the inferior vena cava in a zigzag wave pattern. The distal support hoop 4 comprises a plurality of elongate connector elements 10. Each connector element 10 connects a peak 11 of the wave pattern to an adjacent peak 11 of the wave pattern.

In this case the wave pattern of the distal support hoop 4 comprises six distal peaks 11 and six proximal peaks 11.

The distal support hoop 4 comprises an enlarged end element at each peak 11 of the wave pattern. As illustrated in FIG. 3, in the delivery configuration the diameter of curvature of the end element 11 is greater than the distance between adjacent connector elements 10.

The radial dimension or wall thickness of the distal support hoop 4 is 0.33 mm in this case. The width of each connector element 10 is 0.38 mm in this case.

The support struts 5 extend longitudinally along the internal wall of the inferior vena cava in a curve 14. The support struts 5 connect the proximal support hoop 3 to the distal support hoop 4. In this case the proximal support hoop 3, the distal support hoop 4 and the support struts 5 are formed integrally. The proximal support hoop 3, the distal support hoop 4 and the support struts 5 may be of a shape-memory material, such as Nitinol.

The radial dimension or wall thickness of each support strut 5 is 0.33 mm in this case. The width of each support strut 5 is 0.38 mm in this case.

As illustrated in FIG. 1, the filter 1 comprises twelve capture arms 6 for capturing thrombus passing through the inferior vena cava.

Each capture arm 6 is formed integrally with the proximal support hoop 3. As illustrated in FIG. 4, for each distal peak 11 of the wave pattern a first capture arm 6 is connected to the proximal support hoop 3 at the distal peak 11, and a second capture arm 6 is connected to the proximal support hoop 3 at the distal peak 11.

Each capture arm 6 is movable from the capturing configuration (FIG. 4) to the open configuration (FIG. 8) upon elapse of the predetermined period of time. In the capturing configuration the capture arms 6 are configured to capture thrombus passing through the inferior vena cava towards the heart and the lungs. In the open configuration the capture arms 6 are configured to facilitate unrestricted blood flow.

In the capturing configuration each capture arm 6 extends to an apex 7 in a curve. As illustrated in FIG. 4, for each distal peak 11 of the wave pattern the first capture arm 6 extends from the distal peak 11 to the apex 7 in a first curve 12, and the second capture arm 6 extends from the distal peak 11 to the apex 7 in a second curve 13. The concave portion of the first curve 12 faces inwardly towards the concave portion of the second curve 13. In this manner the capture arms 6 define a generally conically shaped capture region 8 within which thrombus may be captured. Any gaps between adjacent filter elements 6 in the filtration cone 8 are minimised. The filter elements 6 are shape set to maximise filter efficiency.

In this specification, the term curve will be understood to mean a smooth curve or two or more discreet straight sections. For example, the filter element 6 curvature may be heat set to extend towards the apex in a series of two straights. It is appreciated that 2 or more discrete straights, or, a smooth curve, or, a set of smooth curves, may be employed to maximise filter efficiency.

Figure 8:
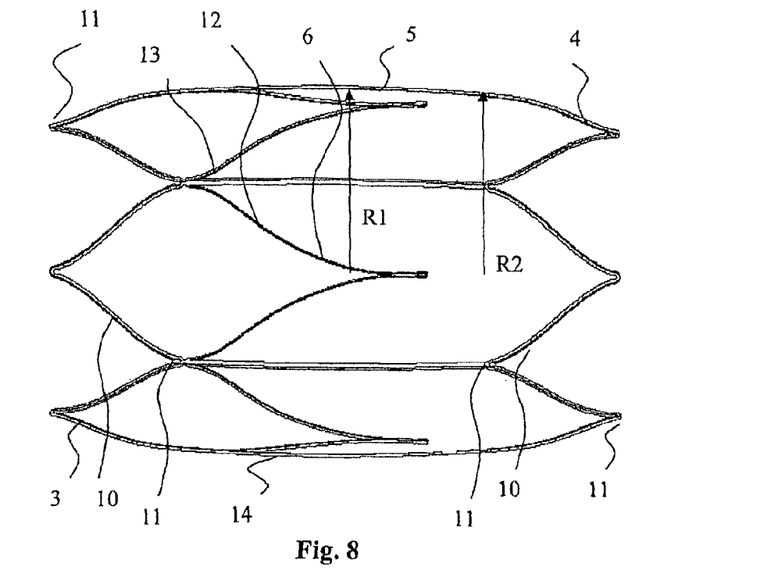
FIG. 8 is a side view of the vascular filter of FIG. 1 in a deployed open configuration.

A perimeter route is defined from a first distal peak 11 of the proximal support hoop 3 along a first connector element 10 to a proximal peak 11 of the proximal support hoop 3, from the proximal peak 11 along a second connector element 10 to a second distal peak 11 of the proximal support hoop 3, from the second distal peak 11 along a first support strut 5 to a first proximal peak 11 of the distal support hoop 4, from the first proximal peak 11 along a third connector element 10 to a distal peak 11 of the distal support hoop 4, from the distal peak 11 along a fourth connector element 10 to a second proximal peak 11 of the distal support hoop 4, from the second proximal peak 11 along a second support strut 5 to the first distal peak 11 of the proximal support hoop 3. A cell is defined within the perimeter route. The filter 1 comprises six such cells. Two capture arms 6 are attached to each cell in both the capturing configuration (FIG. 4) and the open configuration (FIG. 8). This arrangement results in a balanced cell spacing for consistent filtration pore size.

Figure 7:
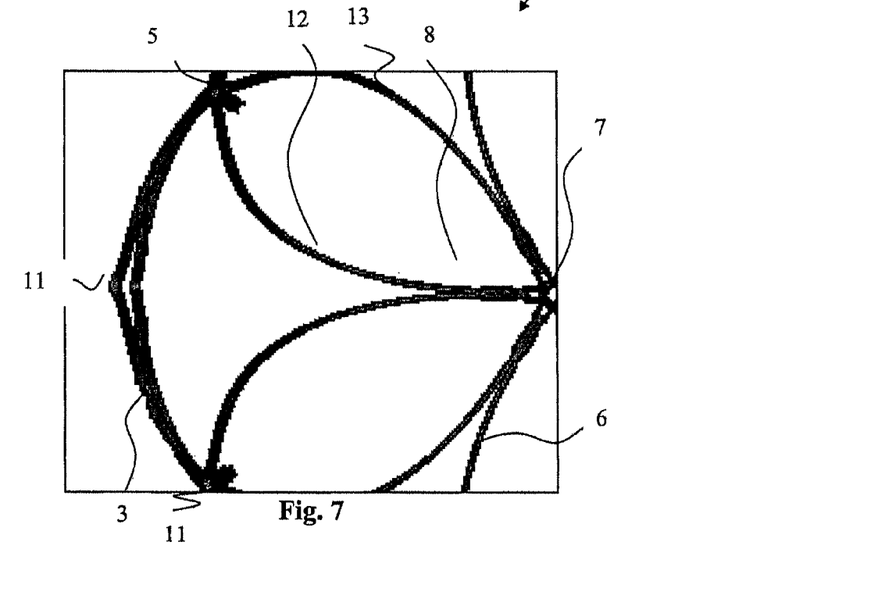
FIG. 7 is an enlarged end view of part of the vascular filter of FIG. 6 in the deployed capturing configuration, FIG. 7(*a*) is an end view of the vascular filter of FIG. 1 during manufacture.
Figure 7A:
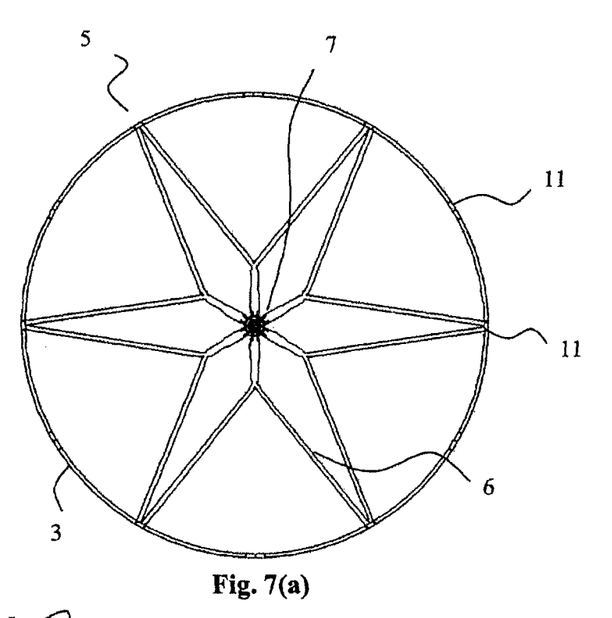
Figure 7B:
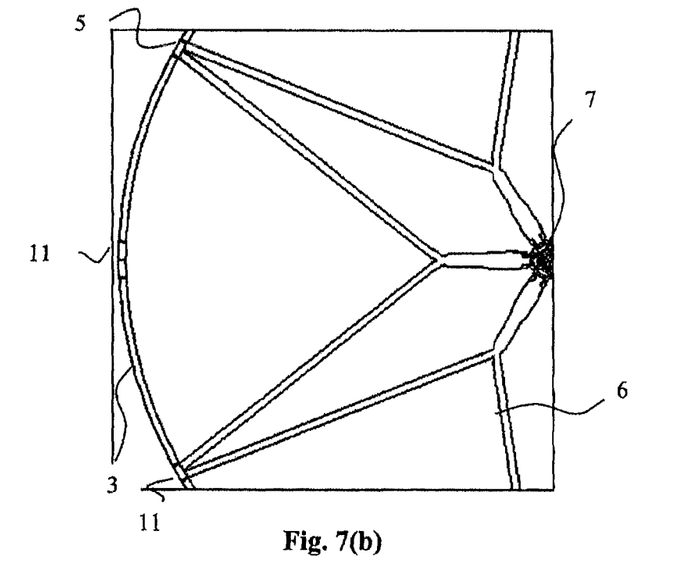
FIG. 7(b) is an enlarged end view of part of the vascular filter of FIG. 7(a) during manufacture.

During manufacture the capture arms 6 are formed into the curved shapes. FIGS. 7(a) and 7(b) illustrate the capture arms 6 before forming into the curved shapes. FIGS. 7(a) and 7(b) illustrate the cut pattern of FIG. 2 expanded without heat setting the capture arms 6.

When the filter 1 is deployed in the inferior vena cava, the apex 7 is substantially in-line with the longitudinal axis extending through the centre of the inferior vena cava, and the capture region 8 is located in the region of the centre of the inferior vena cava. When the filter 1 is deployed in the inferior vena cava, the capture arms 6 extend in the direction of blood flow through the inferior vena cava.

The capture arms 6 are movable from the capturing configuration to the open configuration upon elapse of the predetermined period of time. The capture arms 6 are biased towards the open configuration.

The filter 1 comprises a holder member at the distal ends of the capture arms 6 to temporarily hold the capture arms 6 in the capturing configuration until elapse of the predetermined period of time. The holder member engages with each capture arm 6 to hold the capture arms 6 in the capturing configuration. At least part of the holder member is biodegradable and/or bioabsorbable upon elapse of the predetermined period of time. Upon biodegrading/bioabsorbing of the holder member, the capture arms 6 are free to move from the capturing configuration to the open configuration. The capture arms 6 are not biodegradable or bioabsorbable.

The distal end of the distal support hoop 4 is located distally of the capture arms 6 and the apex 7, and the proximal end of the proximal support hoop 3 is located proximally of the capture arms 6.

When the filter 1 is deployed in the inferior vena cava, the support hoops 3, 4 and the support struts 5 exert a force radially outwardly on the internal wall of the inferior vena cava. In this manner the support hoops 3, 4 and the support struts 5 support the capture arms 6 in position relative to the wall of the inferior vena cava 2.

In the capturing configuration the maximum distance between each support strut 5 and a wall of a blood vessel may be less than 4 mm, and preferably is less than 2 mm. In the capturing configuration the concave portion of the curve 14 of the support struts 5 may face radially outwardly (FIG. 4), or alternatively the support struts 5 may be straight, or alternatively the convex portion of the curve 14 of the support struts 5 may face radially outwardly.

As illustrated in FIG. 8, when the filter is deployed externally of a blood vessel, in the open configuration the convex portion of the curve 14 of the support struts 5 faces radially outwardly. In the open configuration the ratio of R1:R2 is in the range of from 1:1 to 1.5:1 where R1 is the distance of each support strut 5 from the central longitudinal axis of the filter 1 at the point along the support strut 5 where this distance is at a maximum, and R2 is the distance of the support strut 5 from the central longitudinal axis of the filter 1 at an end of the support strut 5 where the support strut 5 is connected to either the proximal support hoop 3 or the distal support hoop 4.

In this case the largest radius R1 of the convex portion of the curve 14 is 17 mm, and the radius R2 of the proximal support hoop 3 and the distal support hoop 4 is 15 mm.

The barrel shape of the filter 1 reduces any bowing or lift-off of the support struts 5 from the blood vessel wall, increases the contact force of the support hoops 3, 4 with the blood vessel, and improves buckling resistance.

In use the filter 1 is collapsed to the delivery configuration (FIGS. 2 and 3), and at least partially loaded into a delivery catheter. The delivery catheter is advanced through the inferior vena cava until the collapsed filter 1 reaches the desired location in the inferior vena cava. A restraining sheath of the delivery catheter is then moved proximally relative to the filter 1 to fully uncover the filter 1. Due to the biasing nature of the filter 1, the filter 1 moves from the collapsed delivery configuration to the expanded deployed configuration (FIG. 4). In the deployed configuration, the support hoops 3, 4 and the support struts 5 exert a radially outward force on the internal wall of the inferior vena cava to support the capture arms 6 in the desired position in the inferior vena cava.

In the event of thrombus passing through the inferior vena cava towards the heart and the lungs, the thrombus will be captured in the capture region 8 of the filter 1. The thrombus will thus be prevented from passing into the heart and the lungs which could otherwise lead to pulmonary embolism. The captured thrombus will gradually be broken down by the body into smaller size particles which will significantly reduce the risk of embolism.

The holder member temporarily holds the capture arms 6 in the capturing configuration until elapse of the predetermined period of time. Upon elapse of the predetermined period of time the holder member biodegrades/bioabsorbs. This enables the capture arms 6 to move from the capturing configuration to the open configuration (FIG. 8). In the open configuration the filter 1 facilitates unrestricted blood flow. The support hoops 3, 4, the support struts 5 and the capture arms 6 remain in the inferior vena cava.

It will be appreciated that the proximal support hoop 3 and/or the distal support hoop 4 may comprise any suitable number of distal peaks and proximal peaks. For example the proximal support hoop 3 and/or the distal support hoop 4 may comprise eleven distal peaks and eleven proximal peaks, or may comprise ten distal peaks and ten proximal peaks, or may comprise nine distal peaks and nine proximal peaks, or may comprise eight distal peaks and eight proximal peaks, or may comprise seven distal peaks and seven proximal peaks, or may comprise five distal peaks and five proximal peaks, or may comprise four distal peaks and four proximal peaks, or may comprise three distal peaks and three proximal peaks.

Figure 9:
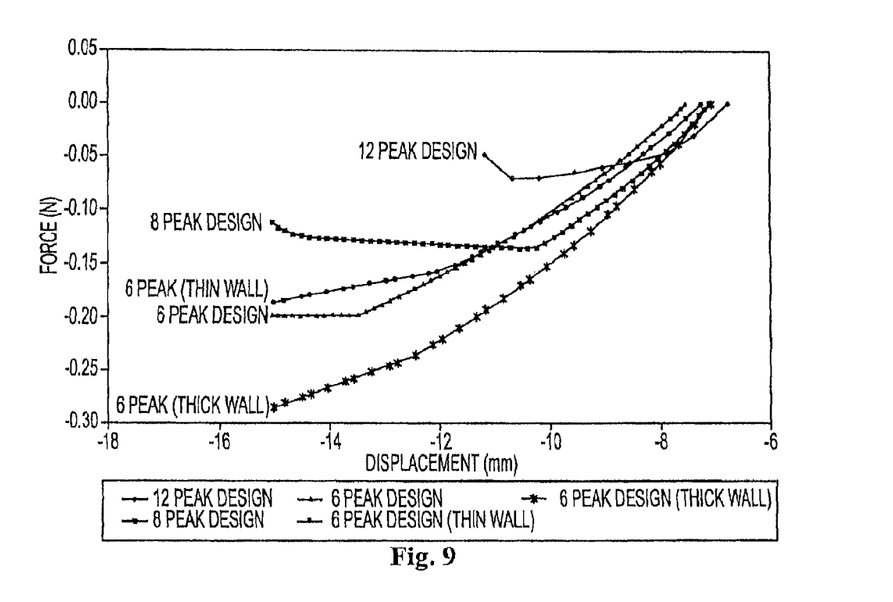
FIG. 9 is a graph of force versus displacement.

FIG. 9 illustrates the buckling behaviour of filters having a different number of peaks. Each filter was placed in a blood vessel having a 16 mm diameter and a crown tip 11 was pulled toward the centre of the blood vessel. The reaction force or force exerted by the filter against this movement is plotted on the graph of FIG. 9. The force and displacement values on the graph are negative as the force is a compressive/pushing force and the crown tip 11 is moving negatively into the centre of the blood vessel.

FIG. 9 illustrates that at the largest displacement the filter having six distal peaks and six proximal peaks exerts a particularly high force against the deformation applied, and thus the filter having six distal peaks and six proximal peaks is highly resistant to buckling.

Figure 10:
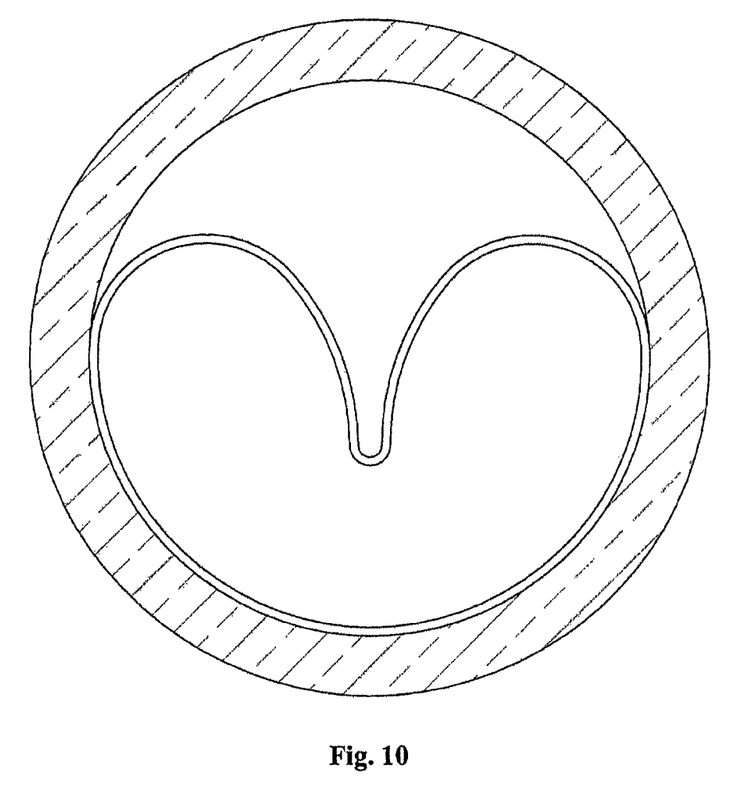
FIG. 10 is an end view illustrating buckling of a vascular filter.

FIG. 10 illustrates buckling of a vascular filter deployed in a blood vessel.

The invention is not limited to the embodiment hereinbefore described, with reference to the accompanying drawings, which may be varied in construction and detail.

The invention claimed is:

1. A vascular filter, comprising:
   capture members configured to capture thrombus passing through a blood vessel, the capture members being movable from a capturing configuration to an open configuration, and
   a support frame for supporting the capture members, the support frame including:
      a proximal hoop, wherein in the capturing configuration, a first capture member extends from a first distal peak of a wave pattern of the proximal hoop towards an apex in a first curve, and a second capture member extends from the first distal peak towards the apex in a second curve, a concave portion of the first curve facing inwardly towards a concave portion of the second curve;
      a distal hoop; and
      connector elements extending from the proximal hoop to the distal hoop, at least one of the connector elements including a lengthwise concavity with respect to a longitudinal axis of the filter when the capture members are in the open configuration and when deployed externally of the blood vessel, the filter including an unrestricted open central channel when the capture members are in the open configuration.

2. The filter of claim 1, wherein the connector elements include a concavity with respect to the longitudinal axis when the capture members are in the capturing configuration.

3. The filter of claim 1, wherein the connector elements extend straight when the capture members are in the capturing configuration.

4. The filter of claim 1, wherein the capture members and the support frame are formed integrally.

5. The filter of claim 1, wherein each connector element connects a peak of the wave pattern of the proximal hoop to a peak of a wave pattern of the distal hoop.

6. The filter of claim 1, wherein the proximal hoop includes an enlarged end element at a peak of the wave pattern of the proximal hoop.

7. The filter of claim 1, wherein the capture members are connected to a distal peak of the wave pattern of the proximal hoop.

8. The filter of claim 1, wherein the capture members join at the apex when in the capturing configuration, the apex being centrally located within the filter and located at a distal end of the capture members.

9. The filter of claim 8, further comprising a biodegradable or bioabsorable holder located at the apex to hold the capture members in the capturing configuration.

10. A vascular filter that moves from a compressed delivery configuration to an expanded capturing configuration, the vascular filter comprising:
    capture members configured to capture thrombus passing through a blood vessel, the capture members being movable from the expanded capturing configuration to an open configuration, and
    support members for supporting the capture members, the support members, in an unconstrained condition, including:
    a proximal hoop extending circumferentially;
    a distal hoop extending circumferentially, the distal hoop being located distal of a distal end of the capture members; and
    connector elements extending from the proximal hoop to the distal hoop, the connector elements being configured to move outward when the vascular filter moves from the compressed delivery configuration to the expanded capturing configuration, the connector elements also being configured to move outward when an inward force exerted by the capture members on the connector elements is removed when the capture members move from the expanded capturing configuration to the open configuration with respect to a longitudinal axis of the filter from the proximal hoop to the distal hoop.

11. The filter of claim 10, wherein each of the capture members is connected to a distal peak of a wave pattern of the proximal hoop.

12. The filter of claim 10, wherein the connector elements extend longitudinally between the proximal and distal hoops.

13. The filter of claim 10, wherein each of the connector elements connects a peak of a wave pattern of the proximal hoop to a peak of a wave pattern of the distal hoop.

14. The filter of claim 10, wherein at least one of the connector elements includes a lengthwise concavity with respect to the longitudinal axis when the capture members are in the open configuration and when deployed externally of the blood vessel.

15. The filter of claim 10, wherein the connector elements extend straight when the capture members are in the expanded capturing configuration.

16. The filter of claim 10, wherein the capture members join at an apex during the expanded capturing configuration, the apex being centrally located within the filter and located at a distal end of the capture members.

* * * * *